United States Patent [19]
Hur et al.

[11] Patent Number: 6,140,363
[45] Date of Patent: Oct. 31, 2000

[54] USE OF ROSMARINIC ACID AND DERIVATIVES THEREOF AS AN IMMUNOSUPPRESSANT OR AN INHIBITOR OF SH2-MEDIATED PROCESSES

[75] Inventors: Eun Mi Hur; Young Bong Choi; Changwon Park, all of Kyonggi-do; Jongsung Lee, Seoul; Dongsu Park, Kyonggi-do; Yungdae Yun, Seoul; Keun Hyeung Lee, Seoul; Jong-Eun Oh, Seoul; Soon Choul Ahn, Taejon-si; Hyun Sun Lee, Taejon-si; Jong Sok Ahn, Taejon-si; Soo Il Jung, Kyonggi-do, all of Rep. of Korea

[73] Assignee: Mogam Biotechnology Research Institute, Rep. of Korea

[21] Appl. No.: 09/312,405

[22] Filed: May 14, 1999

[30] Foreign Application Priority Data

May 16, 1998 [KR] Rep. of Korea ................ 98-17741
May 4, 1999 [KR] Rep. of Korea ................ 99-15989

[51] Int. Cl.$^7$ .................................................. A61K 31/235
[52] U.S. Cl. ............................................. 514/533; 514/570
[58] Field of Search ................................ 514/570, 533

[56] References Cited

U.S. PATENT DOCUMENTS 4,329,361  5/1982  Zenk et al. .
4,354,035  10/1982  Christ et al. ........................ 560/75
4,358,442  11/1982  Wirtz-Peitz et al. ............... 424/199

*Primary Examiner*—James H. Reamer
*Attorney, Agent, or Firm*—Gates & Cooper

[57] ABSTRACT

The present invention relates to use of rosmarinic acid and/or derivatives thereof as immunosuppressive agents and/or as inhibitor of SH2 domain function. Disclosed in the present invention is that rosmarinic acid and derivatives thereof specifically inhibit the binding of ligand peptides to Lck SH2 domain, disturb the Lck-mediated signal transduction in T cells, also inhibit cytoline gene expression, and suppress immune responses in the transplanted tissue. These activities of rosmarinic acid and derivatives thereof support their applicability to treatment, prevention and/or diagnosis of graft rejection, GVHD, autoimmune diseases, inflammatory diseases, etc.

20 Claims, 4 Drawing Sheets

USE OF ROSMARINIC ACID AND DERIVATIVES THEREOF AS AN IMMUNOSUPPRESSANT OR AN INHIBITOR OF SH2-MEDIATED PROCESSES

This application claims the benefit of Korean patent applications number 98-17741, filed May 16, 1998, and number 99-15989, filed May 4, 1999. The entire contents of these applications are hereby incorporated by reference into this application.

Throughout this application various publications are referenced. The disclosures of these publications in their entireties are hereby incorporated by reference into this application in order to more fully describe the state of the art to which this invention pertains.

FIELD OF THE INVENTION

The present invention relates to the use of rosmarinic acid and/or derivatives thereof as immunosuppressant and/or as inhibitor of the Lck (lymphocyte cell kinase) SH2 domain function.

BACKGROUND

Organ transplantation is now common for patients with end-stage renal, cardiac, hepatic or pulmonary failure. Currently, allografts of kidney, heart, lung, liver, bone marrow, pancreas (islet cells), cornea, small intestine and skin are routinely performed. Additionally xenografts are now performed using porcine heart valves. Organ transplants, however, evoke a variety of immune responses in the host resulting in graft rejection and Graft-Versus-Host Disease (hereinafter, referred to as "GVHD").

The immune response is primarily triggered by T cells through recognition of alloantigens, and the major targets in transplant rejection are non-self allelic forms of class I and class II Major Histocompatibility Complex (MHC) antigens. In acute rejection, donor's antigen-presenting cells such as dendritic cells and monocytes migrate from the allograft to the regional lymph nodes, where they are recognized as foreign by the recipient's $CD4^+$ $T_H$ cells, stimulating $T_H$ cell proliferation. Following $T_H$ cells proliferation, a population of effector cells (including cytotoxic $CD8^+$ T cells and $CD4+$ T cells) is generated, which migrates and infiltrates to the graft and mediates graft rejection (Noelle et al., FASEB 5(13):2770, 1991).

Whereas acute rejection is a T cell-dependent process, a broad array of effector mechanisms participates in graft destruction. Through the release of cytokines and cell-to-cell interactions, a diverse assembly of lymphocytes including $CD4^+$ T cells, $CD8^+$ cytotoxic T cells, antibody-forming B cells and other proinflammatory leukocytes, is recruited into the anti-allograft response. Antigen-presenting graft cells are destroyed directly by cytotoxic $CD8^+$ T cells. Activated $CD4^+$ T cells produce interleukin-2 (hereinafter, referred to as "IL-2"), which is essential to the activation of both $CD8^+$ T cells and B cells. Additionally, $CD4^+$ T cells produce other cytokines such as IFN-γ and IL-4 that also contribute to the destruction of allograft. Furthermore, interferon-γ (hereinafter, referred to as "IFN-γ") induces increased expression of class I and class II MHC molecules on graft tissue, which is more readily attacked by alloreactive effector cells. IFN-γ enhances macrophage activity and affects many inflammatory cells leading to delayed-type-hypersensitivity reaction and inflammation causing nonspecific damage to the graft. These reactions appear to be the primary cause of the early acute rejection that may occur within the first few weeks after transplant. If untreated, acute rejection progresses to a rapid and severe process that causes destruction of the transplant within a few days.

In the case of bone marrow transplantation, in particular, GVHD (graft-versus-host disease) is another obstacle to survival of transplanted patient& GVHD is a disease in which transplanted marrow cells attack the recipient's cells (Storb, "Pathophysiology and prevention of graft-versus-host disease." In Advances in Immunobiology: Blood cell antigens and bone marrow transplantation, McCullogh and Sandler, editors, Alan, Inc., N.Y., p.337, 1984). A large proportion of GVHD-afflicted individuals dies as a result of GVHD (Weiden et al., "Graft-versus-host disease in allogeneic marrow transplantation", in Biology of Bone-Marrow Transplantation, Gale and Fox, editors, Academic Press, N.Y., p37, 1980).

To protect patients from such fatal damages, various immunosuppressive agents have been employed. Currently, allograft rejection is controlled using immunosuppressive agents such as cydosporin A, azathioprine, corticosteroids including prednisone, and methylprednisolone) cyclophosphamide. Cyclosporin A, the most powerful and most frequently used immunosuppressant, revolutionized the field of organ transplant surgery. Other immunosuppressive agents such as FK506, rapamycin, mycophenolic acid, 15-deoxyspergualin, mimoribine, misoprostol, OKT3 and anti-IL-2 receptor antibodies, have been used in the treatment and/or prevention of organ transplantation rejection (Briggs, Immunology letters, 29(1–2), 89–94, 1991; FASEB 3:3411, 1989). Although the development of new immunosuppressive drugs has led to substantial improvement in the survival of patients, these drugs are associated with a high incidence of side effects such as nephrotoxicity and/or hepatotoxicity.

Because immune responses in transplantation rejection are primarily dependent on T cell, agents that suppress the functions of T cells are likely to be more efficacious drugs. Cyclosporin A (CsA) and FK506 inhibit T cell activation by inhibiting the transcription of cytokine genes. Their action mechanism can be summarized as follows.

Cyclosporin A and FK506 bind to immunophilins such as Cyclophilins and FK506-binding proteins (FKBPs). The drug-immunophilin complexes bind to and inhibit the enzymatic activity of the Calcium- and Calmodulin-dependent serine/threonine phosphatase, Calcineurin. The inactivation of this enzyme blocks the nuclear translocation of the cytoplasmic component of the transcription factor NF-AT Nuclear factor of activating T cells) required for the expression of cytokine genes including IL-2.

However, Cyclosporin A has associated toxicities and side effects when used even at therapeutic doses. Although FK506 is about 10 to 100 times more potent than Cyclosporin A in inhibiting activation-induced IL-2 transcription in vitro and graft rejection in vivo, it also shows the side effect such as neurotoxicity and nephrotoxicity.

Rapamyycin is another potent immunosuppressant that inhibits IL-2-dependent lymphocyte proliferation. The cellular target of rapamycin-FKBP complex, mTOR has a phosphoinositide kinase activity and the mTOR signaling is related to cell cycle progression in response to cytokines.

All these immunosuppressive drugs described above affect the T cell functions; whereas Cyclosporin A and FK506 block the step of T cell activation, rapamycin inhibits the T cell proliferation. However, the cellular targets of these agents are expressed ubiquitously. Compounds that selectively inhibit the target molecules which is specifically expressed in immune cells, especially T cells, will undoubtedly be an ideal and more efficient immunosuppressive drug, Thus, there presently exists a need for improved immunosuppressive agents acting specifically on immune cells.

Inhibition of T cell activation and effector functions is an attractive target for the development of drugs to treat T cell-mediated immunopathologies, like autoimmune diseases as well as transplant rejection. The antigen-specific T cell activation is initiated by T cell receptor (hereinafter, referred to as "TCR")-mediated signal transduction in which many tyrosine kinases or phosphoproteins are involved. Progression of activated T cells into cell proliferation is subsequently regulated by the interaction between IL-2 and the IL-2 receptor.

A T cell-specific protein tyrosine kinase, Lymphocyte cell kinase (hereinafter, referred to as "Lck") is a key molecule of TCR-mediated signaling and plays an important role in both T cell maturation and activation. The essential role of Lck in the various T cell function is accomplished by the interaction of SH2 and/or SH3 domain with other signaling effector molecules as well as catalytic activity of kinase domain.

SH2 domain, a conserved region in some regulatory proteins, comprises about 100 amino acids and plays a key role in the intracellular communication from a protein to another protein. Many of proteins with SH2 domain have been found to be involved in intracellular signal transduction. The binding specificity between SH2 domain of a protein and its ligand protein is determined by the sequences and structures of phosphotyrosine and nearby amino acids surrounding the binding site (Pawson, Nature, 373: 573–580, 1995).

The SH2 domain in Lck is one of the regulatory motifs of Lck, as is SH3 domain. When Lck is in inactive state, SH2 domain binds to intramolecular phosphotyrosine (Y505). Once Lck is activated, SH2 domain is released from autoregnlative mechanism, that is, the binding site of SH2 domain is exposed to the specific ligand proteins in T cells, allowing them to bind (Peri et al., Oncogene Res., 8: 2765–2772, 1993).

Several previous reports have tested on the key roles of Lck SH2 domain in T cell activation. One of the prominent studies exploited an Lck mutant, in which phosphotyrosine of ligand protein failed to bind to SH2 domain. In this Lck mutant, the signal transduction systems in T cells were found to be disordered, such as the T cell activation-induced calcium signaling and the signaling for the biosynthesis and secretion of IL-2, which are essential to the T cell proliferation (Xu and Littman, Cel, 74: 633–643, 1993; Straus et al., J. Biol. Chem., 271: 9976–9981, 1996; Lewis et al., J. Immunol., 159: 2292–2300, 1997). In summary, the SH2 domain of Lck shows the indispensability for efficient α chain phosphorylation, activation-induced intracellular $Ca^{2+}$ mobilization and IL-2 gene expression in T cells.

Despite of the importance of SH2 domain in cellular signaling, little has been disclosed about the individual SH2 domain function. Study of the roles of tyrosine kinases like Lck in T cell receptor function has been hampered by lack of specific pharmacological inhibitors. Although several kinds of small molecule tyrosine kinase inhibitors such as herbinlycin and PP1/PP2 have been developed, but these drugs inhibit the kinase activity of tyrosine kinase and moreover, lack the specificity.

SUMMARY OF THE INVENTION

We have noted that Lck is specifically expressed in T lymphocyte, and that the SH2 domain of Lck plays a key role in the activation, proliferation and differentiation of T cells. With this notice, we have tried to develop a novel immunosuppressive agent which specifically inhibit the functions of Lck SH2 domain and of T lymphocyte. In the present invention, we disclosed that rosmarinic acid and derivatives thereof efficiently suppress immune responses induced by the transplantation of animal tissue as well as specifically inhibit the SH2 domain of Lck.

Since rosmarinic acid is a kind of domain-specific inhibitor which selectively blocks SH2 domain, it can be used to treat or prevent the diseases or their pathological effects which are mediated by interaction between SH2 domains and their natural ligands, and also used to treat or prevent immune disorder such as organ transplantation rejection, graft-versus-host disease, autoimmune disease and chronic inflammatory diseases.

In accordance with the present invention, there are provided novel use of rosmarinic acid and derivatives thereof as an immunosuppressant.

In addition to the use as an immunosuppressant, this invention provides use of rosmarinic acid and derivatives thereof as an inhibitor of SH2 domain.

In all aspect of this invention, the derivatives of rosmarinic acid include rosmarinyl isopropyl ester, rosmarinyl ethyl ester, and (S)-rosmarinyl bis(tert-butyldimethylsilyl) ether.

This invention also provides use of *Prunella vulgaris* extract as an immunosuppressant.

This invention also relates to use of *Prunella vulgaris* extract as an inhibitor of SH2 domain.

In such aspects of this invention, the immunosuppressant is useful for treatment, prevention, or diagnosis of rejection of transplanted organ or tissue, chronic rejection, or graft-versus-host disease.

In addition, this invention provides use of rosmarinic acid, derivatives thereof or *Prunella vulgaris* extract for treatment, prevention, or diagnosis of autoimmune disease.

This invention also provides use of rosmarinic acid, derivatives thereof, or *Prunella vulgaris* extract for treating a condition characterized by the elevated IL-1β, IL-4 or IL-6 level.

In addition, this invention provides use of rosmarinic acid, derivatives thereof, or *Prunella vulgaris* extract in combination with at least one additional immunosuppressant established.

This invention also relates to method for isolating rosmarinic acid from *Prunelia vulgaris,* comprising the steps of;
1) extracting active material from *Prunella vulgaris* by soaking it in methanol;
2) extracting active fraction with ethylacetate from the product of step 1);
3) purifying the product of step 2) by column chromatography, wherein inactive fraction is washed with solvent comprising chloroform and methanol, and wherein active fraction is eluted with solvent comprising chloroform, methanol, and water,
4) purifying the product of step 3) by chromatography, wherein methanol is employed as developing solvent;
5) purifying the product of step 4) by chromatography, wherein solvent comprising methanol and phosphoric acid is employed as developing solvent; and
6) purifying the product of step 5) by high performance liquid chromatography wherein solvent comprising methanol and phosphoric acid is employed as developing solvent.

It is an object of this invention to provide novel use of rosmarinic acid or derivatives thereof as an immunosuppressant or as an inhibitor of Lck SH2 domain.

It is a further object of this invention to provide an immunosuppressant which can be used with less side effect to mammals.

It is also an object of this invention to provide an immunosuppressant which can specifically inhibit T cell activation, proliferation and/or differentiation.

It is an additional object of this invention to provide an inhibitor of SH2 domain which can suppress intracellular signal transduction of T cell activation.

It is another object of this invention to provide the efficient method for producing rosmarinic acid from *Prunella vulgaris*.

DETAILED DESCRIPTION OF PREFERRED EMBODIMENTS

The present invention provides the use of rosmarinic acid as an immunosuppressant and/or as a specific inhibitor of the Lck SH2 domain. The rosmarinic acid of the present invention includes (R)-rosmarinic acid, (S)-rosmarinic acid and the racemate thereof.

The present invention also provides method for producing rosmarinic acid, wherein rosmarinic acid is isolated from *Prunella vulgaris* by solvent extraction and chromatography procedures.

The present invention also provides the use of derivatives of rosmarinic acid as an immunosuppressant and/or as a specific inhibitor of the Lck SH2 domain. The derivatives of rosmarinic acid include rosmarinyl isopropyl ester, rosmarinyl ethyl ester and (S)-rosmarinyl bis(tert-butyldimethylsilyl)ether.

The present invention also provides pharmaceutical composition, which contains rosmarinic acid, derivatives thereof and/or *Prunella vulgaris* extract. The pharmaceutical composition can be used as immunosuppressant and/or inhibitor of Lck SH2 domain, particularly used for the treatment, prevention and/or diagnosis of the rejection of transplanted organ or tissue, autoimmune diseases, inflammatory diseases, etc.

Hereinafter, the present invention is described in detail.

In one aspect, the present invention provides use of rosmarinic acid, derivatives thereof and/or *Prunella vulgaris* extract as immunosuppressant and/or as specific inhibitor of Lck SH2 domain.

The use of rosmarinic acid in the present invention is discriminated from the established uses or biological activities of rosmarinic acid, as follows; anti-viral activity (WO 9213523), TNF-production inhibitory activity (JP 721584), 5-lipoxygenase inhibitor activity (JP 1121217), antigonadotropic agent DE 3247610, DE 2952114, EP 34214, U.S. Pat. No. 4,329,361, etc.), antioxidant, anti-bacterial activity, etc.

In all aspects of the present invention, rosmarinic acid and derivatives thereof include (R)-rosmarinic acid, (S)-rosmarinic acid, rosmarinyl isopropyl ester, rosmarinyl ethyl ester, (S)-rosmarinyl bis(tert-butyldimethylsilyl)ether, etc. Other derivatives may be used without departing from the scope and spirit of this invention.

In preferred embodiments, rosmarinic acid can be isolated from an extract of various herbs including *Prunella vulgaris*.

Rosmarinic acid is screened to be an inhibitor of the binding between Lck SH2 domain and specific ligand molecule.

In a preferred embodiment, the method for purifying rosmarinic acid from *Prunella vulgaris* comprises the following steps;

1) extracting active material from *Prunella vulgaris* by soaking it in methanol;
2) extracting active fraction with ethylacetate from the product of step 1);
3) purifying the product of step 2) by column chromatography, wherein inactive fraction is washed with solvent comprising chloroform and methanol, and wherein active fraction is eluted with solvent comprising chloroform, methanol and water,
4) purifying the product of step 3) by chromatography, wherein methanol is employed as developing solvent;
5) purifying the product of step 4) by chromatography, wherein solvent comprising methanol and phosphoric acid is employed as developing solvent; and
6) purifying the product of step 5) by high-performance liquid chromatography, wherein solvent comprising methanol and phosphoric acid is employed as developing solvent.

In preferred embodiments, also provided are derivatives of rosmarinic acid, including rosmarinyl isopropyl ester, rosmarinyl ethyl ester and (S)-rosmarinyl bis(tert-butyldimethylsilyl)ether. The derivatives can be synthesized from rosmarinic acid or from tyrosine and caffeic acid, and those skilled in the art will appreciate that more derivatives may be readily synthesized according to the established arts and the present invention.

Figure 1:
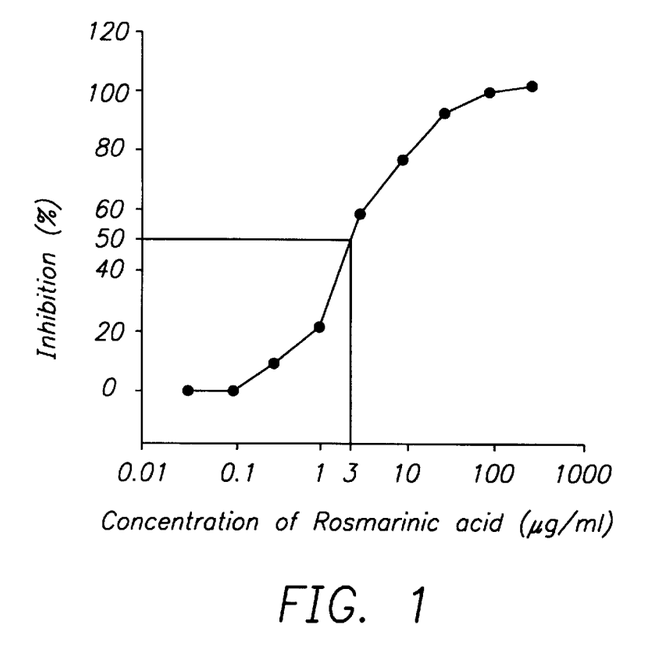
FIG. 1 shows inhibition by rosmarinic acid of binding between the SH2 domain of Lck and the specific phosphotyrosyl peptide in vitro.

In a preferred embodiment, rosmarinic acid and derivatives thereof inhibit in vitro binding between SH2 domain of Lck and specific ligand peptide (see FIG. 1). More particularly, rosmarinic acid and derivatives thereof selectively inhibit the Lck SH2 domain fused with glutathione-S-transferase (GST). Since rosmarinic acid and derivatives thereof interfere with the formation or stabilization of signaling complexes formed by proteins containing one or more SH2 domains and their natural ligands, they can be used to treat or prevent the diseases of their pathological effects mediated by such complexes.

Figure 2:
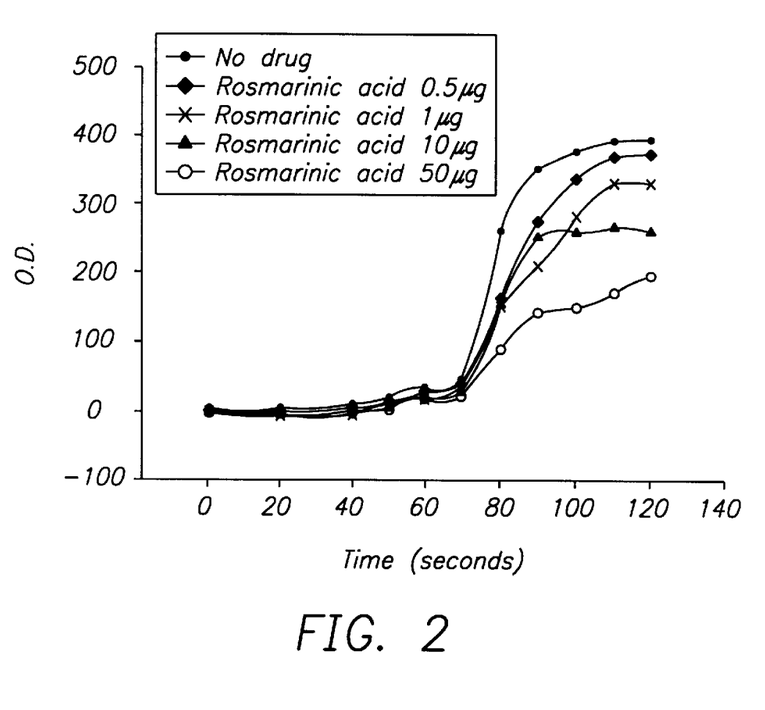
FIG. 2 shows dose dependent suppression by rosmarinic acid of intracellular calcium signaling, which is activated by the application of anti-CD3 and anti-CD4 antibody to Jurkat T cells.

In another preferred embodiment, rosmarinic acid affects the immune response-induced calcium signaling in T cells (see FIG. 2). Particularly, it was reported that the treatment of the antibodies against CD3 and CD4, the surface antigens on T lymphocyte, stimulates T cell activation and subsequent increase of intracellular calcium level, and also known that the action of Lck is involved in these cellular events. Since rosmarinic acid suppresses intracellular calcium signaling activated by anti-CD3 and anti-CD4 antibodies, it is confirmed that it inhibits the function of Lck SH2 domain and also can be used to suppress the process of T cell activation.

In still another preferred embodiment, rosmarinic acid and derivatives thereof inhibit IL-2 gene expression in T cells. The present invention employs IL-2/luciferase reporter system as an assay for IL-2 gene expression level. Since the biosynthesis and secretion of IL-2 leads to T cell proliferation, rosmarinic acid and derivatives thereof which inhibit IL-2 synthesis can be used to suppress T cell proliferation.

Based on such findings, rosmarinic acid and derivatives thereof can be used not only to inhibit the binding to SH2 domain of Lck and the biosynthesis of IL-2, but also to suppress the immune responses and diseases in which the functions of SH2 domain and IL-2 involve.

Figure 5:
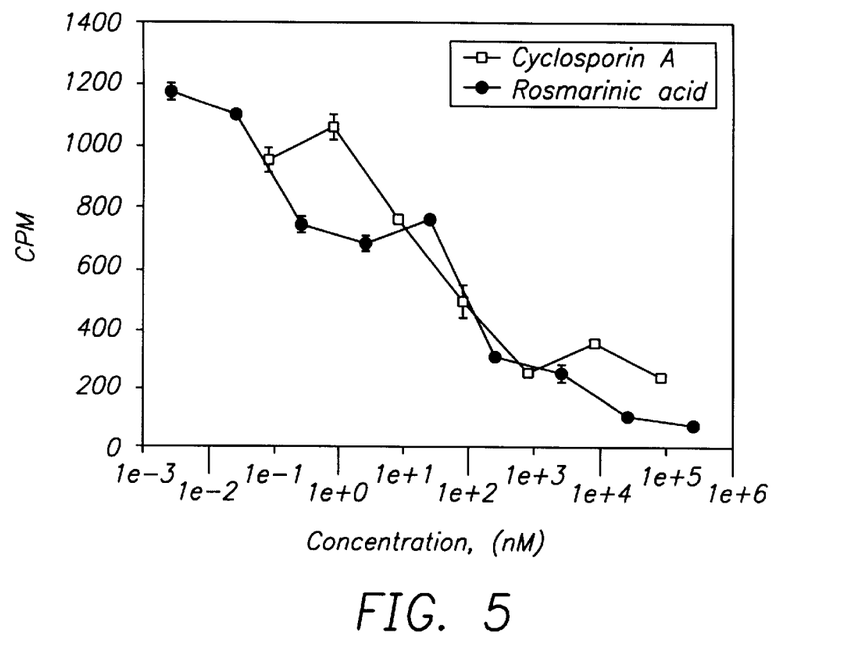
FIG. 5 shows inhibition by rosmarinic acid of T cell proliferation in Mixed Lymphocyte Reaction (MLR)
Figure 6:
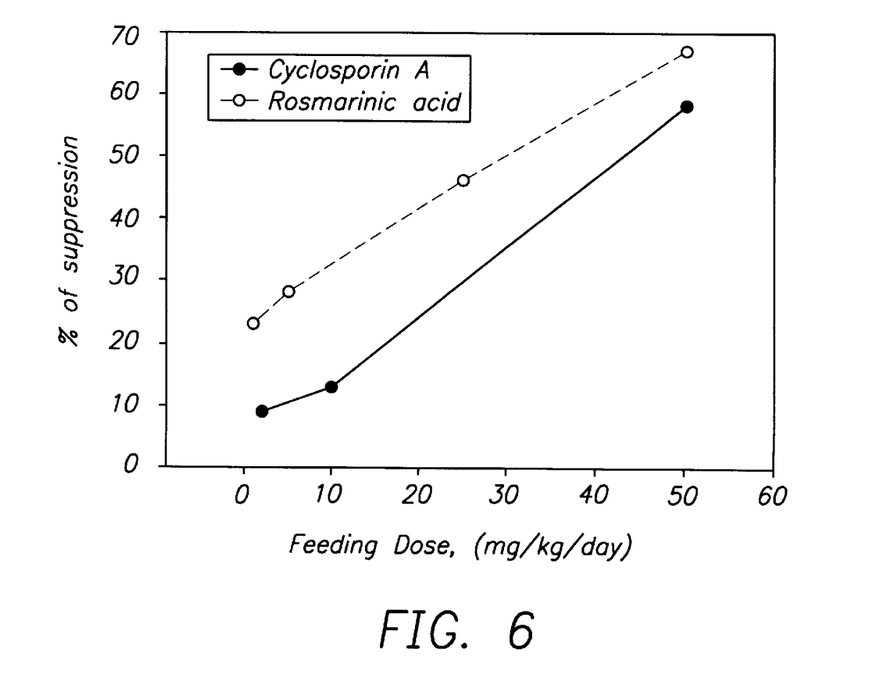
FIG. 6 shows the suppressive effect of rosmarinic acid on contact sensitivity response to DNFB in mice.
Figure 7:
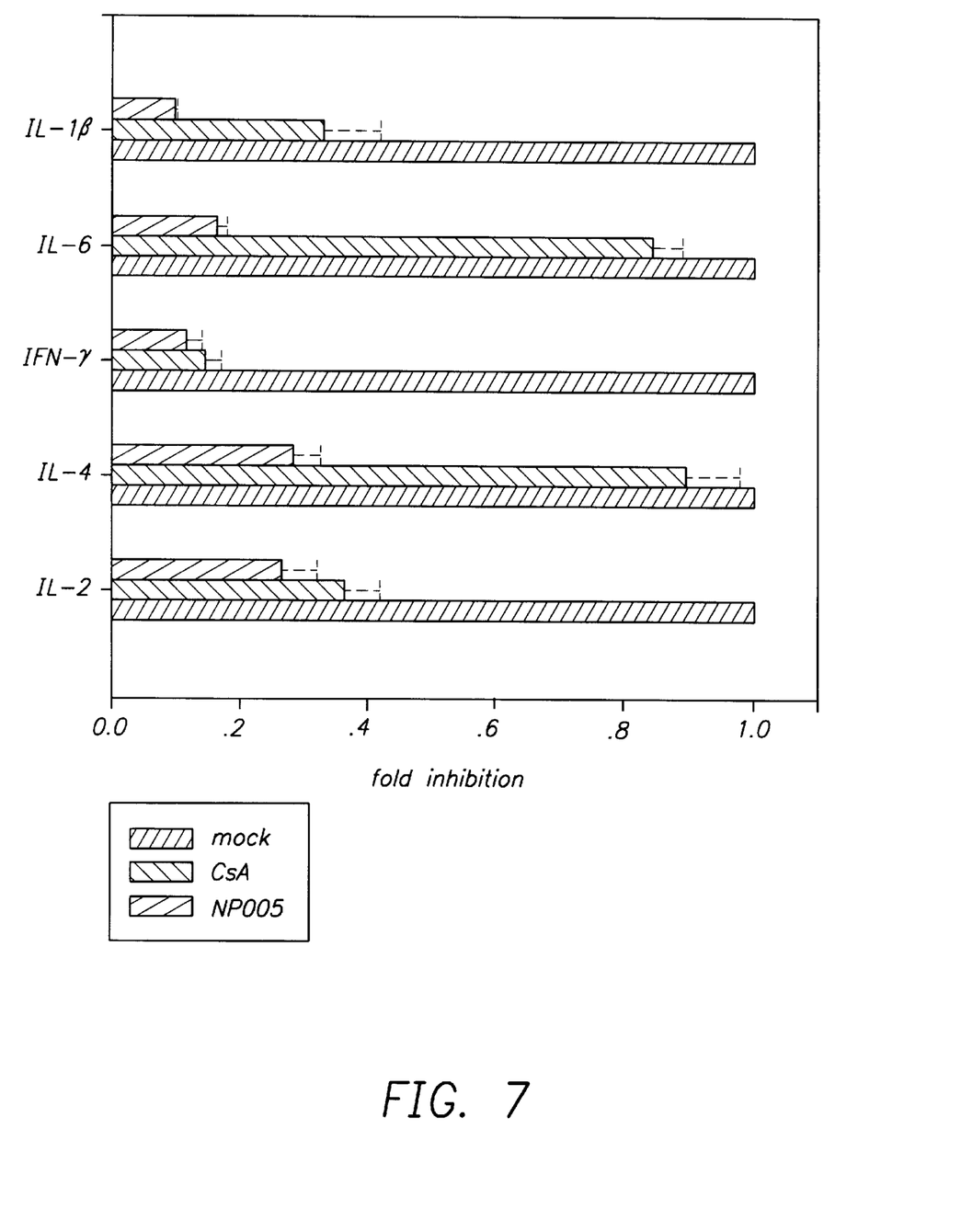
FIG. 7 shows the suppressive effect of rosmarinic acid on cytokine production of renal allografts.

According to preferred embodiments, rosmarinic acid and derivatives thereof suppress immune response in vitro (see FIG. 5) and in vivo (see FIG. 6). In the present invention, Mixed Lymphocyte Reaction (MLR) and contact hypersensitivity response to DNFB are performed to verify the immunosuppressive activities of rosmarinic acid and derivatives thereof.

According to another preferred embodiment, rosmarinic acid and derivatives thereof suppress allograft rejection in animals (see table 1). In the present invention, this suppressive effect is confirmed by in vivo pharmacological test procedure, in which the survival duration of grafted skin is measured.

According to still another preferred embodiment, rosmarinic acid suppresses the transplantation-induced gene expression of various cytokines. Since it has been discovered that cytokine genes are expressed at higher level in allograft tissues, the ability of rosmarinic acid to suppress the production of cytokines was examined using the method Reverse Transcription—Polymerase Chain Reaction (RT-PCR). The result implicates that rosmarinic acid and derivatives thereof are applicable to immunosuppression therapy for transplantation rejection and to treatment of other diseases caused by the elevation of various cytokine levels.

Based on such results, rosmarinic acid and derivatives thereof are useful in the treatment of transplantation rejection such as heart, kidney, liver, bone marrow and skin transplants; autoimmune diseases such as lupus, rheumatoid arthritis, diabetes mellitus, myasthenia gravis, multiple sclerosis and psoriasis; diseases of inflammation such as dermatitis, eczema, seborrhea and inflammatory bowel disease; and fungal infections.

The present invention also provides pharmaceutical composition containing rosmarinic acid, derivatives thereof and/or *Prunella vulgaris* extract.

The composition is employed in immunosuppressive therapy, particularly in therapy for transplantation rejection, autoimmune disease and inflammatory disease.

In a preferred embodiment, the composition can be used for the treatment, prevention and/or diagnosis of transplantation rejection, autoimmune disease and inflammatory disease, more specifically of GVHD, lupus, rheumatoid arthritis, diabetes mellitus, myasthenia gravis, multiple sclerosis, psoriasis, dermatitis, eczema, seborrhea, inflammatory bowel disease, Crohn's disease, primary biliary cirrhosis, etc.

In another preferred embodiment, the composition can be used for inhibiting the functions of SH2 domain of Lck or SH2-mediated cellular functions. The composition includes a therapeutically effective amounts of rosmarinic acid, derivatives thereof and/or *Prunella vulgaris* extract, within/without a pharmaceutically acceptable delivery vehicle. Moreover, the compositions may include other immunosuppressant drug(s), such as cyclosporin A and derivatives thereof, FK-506 and derivatives thereof, mycophenolic acid and 2-(N-morpholino)ethyl ester thereof, mycophenolate mofetil, azathioprine, corticosteroids, reflunornide, cyclophosphamide, rapamycin, OKT-3, ATG, 15-deoxyspergualin, mizoribine, misoprostol, methotrexate, anti-interleukin-2 receptor antibodies and anti-lymphocyte/thymocyte antisera. The composition including additional immunosuppressant shows synergism, that is, it has an increased immunosuppressive activity relative to the sum of the effects produced by rosmarinic acid or other immunosuppressant drug used alone, allowing greater immunosuppressive activity with reduced toxicity.

In another preferred embodiment, the composition is used for treating transplantation rejection. In this regard, the composition can be used for treating rejection of an allograft or a xenograft, or complications caused by graft-versus-host disease. In a further embodiment, the composition used for treating transplantation rejection includes rosmarinic acid and cyclosporin A.

Rosmarinic acid and the derivatives thereof may also be administered in combination with one or more nonsteroidal anti-inflammatory agent, selected from the group including aspirin, ibuprofen, naproxen, indomethacin, didofenac, sulindac, piroxicam, etodolac, ketoprofen, meclofenamate, suprofen and tolmetin, for the treatment and/or prevention of organ transplantation rejection, graft-versus-host disease, autoimmune diseases and chronic inflammatory diseases in a mammal.

Rosmarinic acid, derivatives thereof and/or *Prunella vulgaris* extract may be formulated with a pharmaceutical vehicle or diluent for oral, intravenous, subcutaneous, intranasal, intrabronchial or rectal administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds of the present invention may also be employed with sodium lauryl sulfate or other pharmaceutically acceptable detergents to enhance oral bioavailability of such compounds.

Rosmarinic acid and derivatives thereof may be administered in a dosage ranges of about 0.01~1000 mg/kg, preferably 0.1~500 mg/kg, and may be administered 0.5~3 times a day.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Screening inhibitor of binding to Lck SHE domain

A novel screening system was developed in the present invention to screen a substance inhibiting the interaction between Lck SH2 domain and its ligand. In the binding assay, Lck SH2 domain expressed and purified as a fusion protein with Glutathione-S-transferase (GSI) were covalently attached to 96-well microtitre plates through amide bond formation. The immobilized proteins were subsequently allowed to bind biotinylated phosphotyrosine (Y)-containing synthetic peptide (biotin-SGSGEEPQpYEEIPI) known as a high affinity ligand for the Lck SH2 domain.

For attachment to 96-well microtitre plate, 1 μM of purified fusion protein (GST-Lck SH2) was reacted for 2 hours at room temperature. Added to the binding assay were 1 μM of the biotinylated synthetic peptide (the ligand of Lck SH2 domain) and a candidate for the inhibitor. The candidates were thousands of natural products including various kinds of Streptoryces, fungi and herbs extract. Binding reaction was performed for 2 hours at room temperature, allowing the competitive inhibition of the binding between GST-Lck SH2 and the peptide ligand. Then peroxidase-conjugated streptavidin (Pierce, USA) was added into the mixture so that added conjugates can be bound to biotinylated peptide. After unbound conjugates were washed, coloring reaction was performed to measure the activity of immobilized peroxidase, or the binding activity of the peptide to SH2 domain in the presence of the candidate added. More particularly, the coloring reaction was initiated by adding 3,3,5,5-tetramethyl benzidine (substrate) to the reaction mixture. After 30 minutes, the reaction was stopped by adding 0.8M sulfuric acid, and immediately brought to the spectrophotometry of measuring absorbance at 450 nm.

This screening procedure resulted in the discovery of an inhibitory substance, which was isolated from a perennial herb Prunella vulgaris.

Example 2

Isolation and purification of rosmarinic acid from Prunella vulgaris extract

Dried Prunella vulgaris (600 g) purchased from local herbalist was soaked in methanol (10~20L) at room temperature. After 3–5 days, methanol extract was concentrated in vacuum, resuspended in distilled water, and extracted in ethylacetate. The ethylacetate extract was fractionated based on inhibitory activity of binding to SH2 domain of Lck.

The fraction with highest activity was concentrated in vacuum and dissolved in small dose of chloroform:methanol (20:1), and then loaded into silica gel column chromatography After the fraction without the inhibitory activity was washed with chloroform: methanol (20:1), active fraction was eluted with chloroform: methanol: water (20:10:1~10:5:1).

The active fraction was concentrated in vacuum, dissolved in small volume of methanol, and then loaded into Sephadex LH-20 (Sigma), using methanol as developing solvent.

The resulting active fraction was brought to reverse phase low pressure chromatography (Lobar, Merck), using 20% methanol and 1% phosphoric acid as developing solvent. The active fraction absorbed in Diaion HP-20 was eluted with 100% methanol.

The eluted fraction was loaded to high-performance liquid chromatography (HPLC), in which 45% methanol and 5% phosphoric acid solution was used as developing solvent through YMC-Pack C18 column (2 cm inner diameter×15 cm outer diameter), with 4 ml/min of flow rate and 254 nm of UV wavelength. The active fraction with 22 minutes of elution time had peaked in the level of inhibitory activity of binding to SH2 domain. This fraction was absorbed in diaion EP-20 and eluted with 100% methanol, so that inhibitory substance (50 mg) for binding to SH2 domain of Lck can be obtained.

The physical and chemical properties of the purified product were shown as follows;

1) appearance: liquid with light green color
2) UV, $\lambda_{max}$ (nm) : 210, 220, 230 (s), 250 (s), 285, 340 (neutral and acid methanol), 208, 225, 250–260, 300–310, 370 (basic methanol)
3) IR, $v_{max}$ (cm$^{-1}$, KBr): 3300 (hydroxyl, 1700 (carbonyl), 1600, 1500, 1450 (aromatic)
4) mass spectrum: m/z 361[M+H]
5) $^1$H-NMR (300 M DMSO), δ(ppm): 7.5 (1H, d, J=15.8 Hz, H-8), 7.03 (1H d, J=2.3 Hz, H-2), 6.92 (1H, dd, J=23, 8.3 Hz, H-6), 6.76 (1H, d, J=83 Hz, H-5), 6.77 (1H, d, J=2.3 Hz, H-2'), 6.67 (1H, d, J=8.3 Hz, H-5'), 6.62 (1H, dd, J=23, 8.3 Hz, H-6'), 6.25 (1H, d, J=15.8 Hz, H-7), 6.62 (1H, dd, J=3, 9.8 Hz, H-8'), 3.10 (1H, dd, J=3, 14.3 Hz, H-7α), 2.93 (1H, dd, J=9.8, 14.3 HZ, H-7β)
6) $^{13}$C-NMP (75 MHz, DMSO), δ (ppm): 127.9 (C-1), 115.6 (C,2), 149.4 (C-3), 146.7 (C-4), 116.5 (C-5), 122.9 (C-6), 146.7 (C-7), 115.6 (C-8), 169.1 (C-9), 131.1 (C-1'), 117.5 (C-2'), 145.9 (C-3'), 144.8 (C-4'), 116.2 (C-5'), 121.8 (C-6'), 38.79 (C-7'), 77.6 (C-8'), 177.9 (C-9').

Formula 1

As a result, the purified molecule proved to be rosmarinic acid.

Example 3

Rosmarinyl isopropyl ester

To rosmarinic acid (75mg, 0.21 mmol) dissolved in DMF (4 mL), isoprophylalcohol (33 mg, 0.26 mmol) and O-benzotriazol-yl-N,N,N'N'-tetramethyluronium tetrafluorborate (TBTU, 75 mg 0.23 mmol) were added. After the solution was stirred at room temperature under $N_2$ atmosphere, methylbenzeneamine (34 mg, 0.28 mmol) was added. Stirred at room temperature for 24 hours, the reaction solution was diluted with ethylacetate 50 ml and washed with NaHCO$_3$ solution (3×20 ml) and 10% HCl. The organic phase was dried on MgSO$_4$ and concentrated in vacuum. The yellow solid (79 mg, 82%) was obtained by flash chromatography (elution system, n-Hexane: ethyl acetate, 85:15 to 6:4).

Formula 2

Example 4

Rosmarinyl ethyl ester

Rosmarinic acid (75 mg, 0.21 mmol) in ethanol (10 mL) was refluxed for 24 hour. The solution was diluted with ethylacetate 50 ml and washed with saturated NaHCO₃ solution (3×20 ml) and 10% HCl. The organic phase was dried on MgSO₄ and concentrated in vacuum. The white solid (79 mg, 82%) was purified by flash chromatography (elution system, n-Hexane: ethyl acetate, 85:15 to 6:4).

Formula 3

(R or S)

Example 5
(S)-rosmarinyl bis(tert-butyldimethylsilyl) ether (step 1) Acetylation of hydroxylphenylalanine HCl salt (1)

To (S)-tyrosine (1.45 g, 80 mmol) dissolved in nitrobenzene (40 ml) distilled previously, AlCl₃ (4.24 g, 31.8 mmol) was slowly added. The resulting solution was stirred, and after acetylchloride (0.78 ml 11 mmol) was added, the solution was refluxed for 6 hours The reaction solution was poured into concentrated HCl solution containing ice and 80 ml of ethylacetate was added and the organic phase was separated and dried in vacuum. The solid product was recrystallized in 5M HCl solution.

$^1$H NMR (D₂O): δ 2.67 (s, 3H, 3.22 (dd, 1H, 3.32 (dd, 1H, 4.27 (dd, 1H), 7.00 (d, 1H), 7.49 (dd, 1H), 7.82 (d, 1H);

Mass spectrum m/z: 223 ([M]-HCl)⁺

Reaction Formula 1

(step 2) Synthesis of acetyl hydroxylphenyl lactic acid (2)

The compound (1) (1 g, 3.5 mmol) was dissolved in water (20 ml) and cooled in ice-water bath. This solution was dropwisely added into NaNO₂ (0.4g, 5.8 mmol) dissolved in water 12 ml and slowly stirred. After the solution was stirred at room temperature for 20 hours, ammonium sulfate (204 mg, 1.54 mmol) was added and stirred for further 1 hour. The crude product was extracted in ethylacetate, and the separated organic phase was dried on MgSO₄. Excess solvent was removed by rotary evaporator. Flash chromatography (elution system, n-Hexane: ethyl acetate, 85:15 to 6:4) gave yellow oil as a major product (0.7 mg, 81%).

$^1$H NMR (CDCl₃): δ 2.62 (s, 3H, 2.97 (dd, 1H, 3.16 (dd, 1H, 4.50 (dd, 1H, 6.92 (d, 1H), 7.37 (dd, 1H), 7.63(d, 1H, 12.16 (s, 1H);

Mass Spectrum m/z 224(M⁺)

Reaction Formula 2

(step 3) Synthesis of 3-(3,4-dihydroxyphenyl)-(S)-lactic acid (3)

Compound (2) (1 g, 4.5 mmol) was added into 30% H₂O₂ solution containing NaOH (0.64 g, 16 mmol) and the solution was stirred for 12 hours. The resulting solution was acidified with concentrated HCl (1 ml) and the crude product was extracted with ethylacetate. The separated organic phase was dried on MgSO₄ and concentrated by rotary evaporator. The yellow solid was obtained by flash chromatography (0.55 mg, 61%).

$^1$H-NMR (acetone-d₆) δ 2.78 (dd, 1H), 2.97 (dd, 1H), 4.32 (dd, 1H, 6.60 (dd, 1H), 6.71 (d, 1H, 6.78 (d, 1H;

mass spectrum m/z 198 (M⁺)

Reaction Formula 3

(step 4) Synthesis of diallylether allylester of 3-(3',4'-dihydroxyphenyl)-(S)-lactic add (4)

Compound (3) (940 mg, 4.7 mmol) was dissolved in acetone (14 mL), and then allylbromide (7 mL, 80 mmol) and potassium carbonate (1.97 g, 14.3 mmol) were added. The solution was refluxed in silicon-oil bath for 22 hours. Insoluble salt was filtered and the filtrate was dissolved in $CH_2Cl_2$ and washed with $H_2O$ (10 mL), and the organic phase was dried on $MgSO_4$ and concentrated The colorless solid was obtained by flash chromatography (640 mg, 42%).

$^1$H-NMR ($CDCl_3$) δ 2.91 (dd, 1H, 3.06 (dd, 1H), 4.44 (dd, 1H, 4.58 (d, 4H), 4.65 (dt, 2H), 5.23–5.44 (m, 2H, 5.84–5.97 (ddt, 1H, 6.01–6.14 (m, 1H, 6.73 (dd, 1H), 6.78 (d, 1H), 6.82 (d, 1H);

mass spectrum m/z: 318 (M$^+$)

(step 5) Synthesis of bis(tert-butyldimethylsilyl)ether of caffeic acid (5)

To caffeic acid (4 g, 22.2 mmol) dissolved in $CH_2Cl_2$, tert-butyldimethylsilyltriflate and triethylamin were added, and the solution was stirred for 17 hours. The reaction solution was washed with 10% HCl solution (2×20 ml) and water (2×20 ml). The organic phase was dried on $MgSO_4$ and concentrated. The colorless solid was purified by flash chromatography and dissolved in 50% methanol (200 ml). After potassium carbonate (1.8 g, 11 mmol) was added, the reaction solution was stirred at room temperature for 6 hours. The solid was removed by filtration, and then the filtrate was acidified with a small dose of hydrochloric acid. After the acidified product was extracted with ethylacetate and washed with water (3×20 ml), the combined organic phase was dried on $MgSO_4$ and concentrated. The colorless solid was obtained by flash chromatography.

R = TBDMS (step 6) Reaction of bis(tert-butyldimethylsilyether of caffeic acid and 3-(3',4'-dihydroxyphenyl)-(S)-lactic acid (6)

The purified bis(tert-butyldimethylsilylether of caffeic acid (5) (4.31 g, 10.5 mmol) was reacted with $SOCl_2$ (2.4 mL, 33 mmol) in $CCl_4$ and excess solvent was removed. The synthesized compound (4) (2.13 g, 6.0 mmol) in $CH_2Cl_2$ and trethylamine (5.9 ml, 42 mmol) were added and stirred in $N_2$ atmosphere for 4 hours. The produced solution was washed with 10% HCl solution and brine. The separated organic phase was dried on $MgSO_4$ and concentrated. By using flash chromatography (20% ethylacetate in hexane), bright yellow solid was obtained (4.6 g, 90%).

Reaction Formula 6

R = TBDMS
R' = CH₂CH═CH₂

(step 7) (S)-Rosmarinyl bis(tert-butyldimethylsilyl)ether (7)

The purified solid (6) (600 mg, 1.2 mmol) was dissolved in 30 ml of ethanol, benzene, water (7:3:1, v/v), the solution was refluxed in the presence of tris(triphenylphosphine)rhodium(I)chloride (700 mg, 0.757 mmol). The excess solvent was removed the remainder was dissolved in ethylacetate (40 ml). The organic phase was washed with 40 ml of saturated NaHCO₃ solution (3×20 ml) and 10% HCl. The organic phase was dried on MgSO₄ and concentrated. Flash chromatography (elution system, n-Hexane:ethyl acetate, 85:15 to 6:4) gave colorless solid (120 mg, 29%).

¹H-NMR (CDCl₃) δ 0.22 (s, 6H), 0.23 (s, 6H), 0.99 (s, 9H), 1.00 (s, 9H), 3.03 (dd, 1H), 3.13 (dd, 1H), 5.22 (dd, 1H), 6.29 (d, 1H), 6.67 (dd, 1), 6.75 (d, 1H), 6.86 (m, 2H), 7.05 (dd, 1H), 7.16 (d, 1H), 7.56 (d, 1H);

Mass Spectrum m/z 592([M]+H)⁺

Reaction Formula 7

Example 6
Synthesis of (S)-rosmarinic acid

The purified solid obtained in the Example 5(4.23 g, 5.97 mmol) was dissolved in THF in N₂ atmosphere and tetra-n-butylammonium fluoride (1.0M in THF, 12 mL, 12 mmol) was added. After stirred for 15 minutes, the solution was washed with water and extracted with ethylacetate. The separated organic phase was dried on MgSO₄ and concentrated. Flash chromatography gave yellow oil as a major product (1.47 g, 51%).

¹H NMR (acetone-d₆) δ 3.03 (dd, 1H, 3.13 (dd, 1H), 5.22 (dd, 1H), 6.29 (d, 1H), 6.67 (dd, 1H), 6.75 (d, 1H), 6.86 (m, 2H), 7.05 (dd, 1H), 7.16 (d, 1H), 7.56 (d, 1H);

mass spectrum m/z 361[M+H]⁺)

Reaction Formula 8

The following Examples illustrate the efficacy of rosmarinic acid and derivatives thereof as an inhibitor of Lck SH2 domain or as an immunosuppressant.

However, it will be appreciated that those skilled in the art, on consideration of this disclosure, may make modifications and improvements within the spirit and scope of the present invention.

Example 7
Inhibition of in vitro binin between Lck SH2 domain and specific phosphotyrosyl peptide The activities of rosmarinic acid and derivatives thereof to bind SH2 domain of Lck were investigated in this invention by using the in vitro binding assay system of Example 1.

Various concentrations (0.03~300 µg/ml) of rosmarinic acid solution, which was isolated from *Prunella vulgaris* or derivatives thereof, were added to the protein-coated microwell mixed with phosphopeptide solution. The binding of biotiyated pY peptides was detected by the streptavidin-conjugated horseradish peroxidase (HRP).

Rosmarinic acid selectively bound to GST-fused SH2 domain of Lck, proportionally to the concentration (see FIG. 1). The estimated half-maximal inhibitory concentration ($IC_5$) value was 3 μg/ml.

In addition to treatment of rosmarinic acid, treatment of derivatives of rosmarinic acid such as rosmarinyl isopropyl ester, rosmarinyl ethyl ester and (S)-rosmarinyl bis(tert-butyldimethylsilyl)ether and (S)-rosmarinic acid resulted in a competitive inhibition of binding to SH2 domain. In these cases, $IC_{50}$ were 1, 4, 13 and 10 μg/ml, respectively.

Rosmarinic acid and derivatives thereof are, therefore, useful as reagents for biological research since, for example, they can uncouple or block a particular signal transduction pathway of interest. Rosmarinic acid and derivatives thereof, which interfere with the formation or stabilization of signaling complexes formed by proteins containing one or more SH2 domains and their natural ligands, could be used to treat or prevent the pathological diseases mediated by such complexes.

Example 8

Inhibitory effect on the Signal transduction of T cell proliferation

Since rosmarinic acid isolated from *Prunella vulgaris* and derivatives thereof inhibit binding of ligands to SH2 domain of Lck, it is supposed that these inhibitory effects will disturb the signal transduction system of T cell proliferation, changing the pattern of intracellular calcium mobilization.

The antigen-specific T cell activation is initiated by TCR-mediated signal transduction in which many tyrosine kinases or phosphoproteins are involved. The progression of activated T cells into cell proliferation is subsequently regulated by the interaction between IL-2 and the IL-2 receptor. Particularly, it was reported that the treatment of the antibodies against CD3 and CD4, the surface antigens on T lymphocyte, stimulates T cell activation and subsequent increase of intracellular calcium level, and also known that the action of Lck is involved in these cellular events. Therefore, it was investigated in the present invention whether rosmarinic acid could inhibit the increase of intracellular calcium level, which was induced by T lymphocyte activation.

Fura-2/AM (Calbiochem, San Diego, Calif., USA), a fluorescent indicator of intracellular calcium, was loaded into Jurkat cells, and various amounts (0.5 μg, 1 μg, 10 μg, 50 μg) of rosmarinic acid, isolated from *Prunella vulgaris*, was treated to the cells for 10 minutes. The cells were treated with anti-CD3 and anti-CD4 antibodies, and then the fluctuation of intracellular calcium level was recorded by the amount of fluorescence emitted from the cells.

FIG. 2 shows the dose-dependent inhibitory effect of rosmarinic acid on the calcium level. Thus, it was disclosed that rosmarinic acid, isolated from *Prunella vulgaris* in the present invention, has an inhibitory activity to intracellular calcium mobilization.

Example 9

Inhibition of TCR stimulation-induced IL-2 gene expression

Since rosmarinic acid and derivatives thereof selectively inhibit Lck function, we tested whether these compounds could suppress the IL-2 activation-induced IL-2 production, which is responsible for the progression into T cell proliferation. The effects of rosmarinic acid and derivatives thereof on the level of IL-2 gene expression were tested by using the IL-2-luciferase reporter system, in which cultured cells were transfected with a reporter plasmid. The plasmid was constructed by fusion of the IL-2 promoter sequence with the structural gene of luciferase.

$10^6$ Jurkat T cells were transfected with IL-2-luciferase reporter plasmid by use of Superfect™ (Qiagen Inc.). After incubation for 24 h, cells were treated with various drugs (8 μM rosmarinic acid or derivatives thereof, 8 μM Cyclosporin A, 8 μM FK506, 8 μM LY294002) for 30 min prior to T cell activation. Cells were activated by incubation for 14 h on a 35 mm dish coated with 5 μg/ml anti-CD3 antibody (UCHT1, Pharmingen) and/or anti-CD4 antibody (RPA-T4, Pharmingen) and then harvested. For PMA plus Iononycin stimulation, 5 ng/ml of PMA and 500 ng/ml of Ionomycin were added to the culture media and incubated for 14 h. Luciferase activity was determined three times in duplicate for each experiment with a Berthold luminometer LB953.

Figure 3:
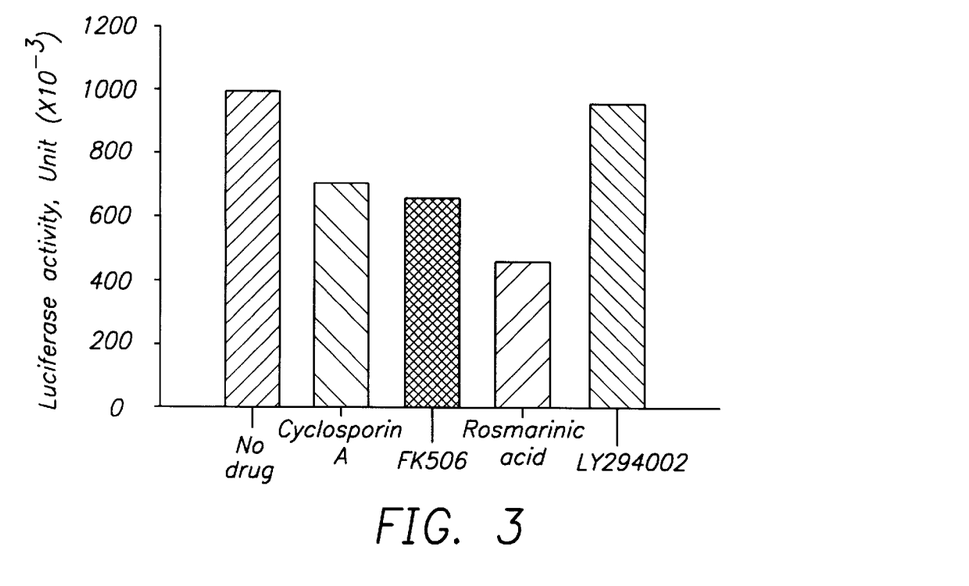
FIG. 3 shows the suppressive effect of rosmarinic acid on TCR-stimulated T cell activation.
Figure 4:
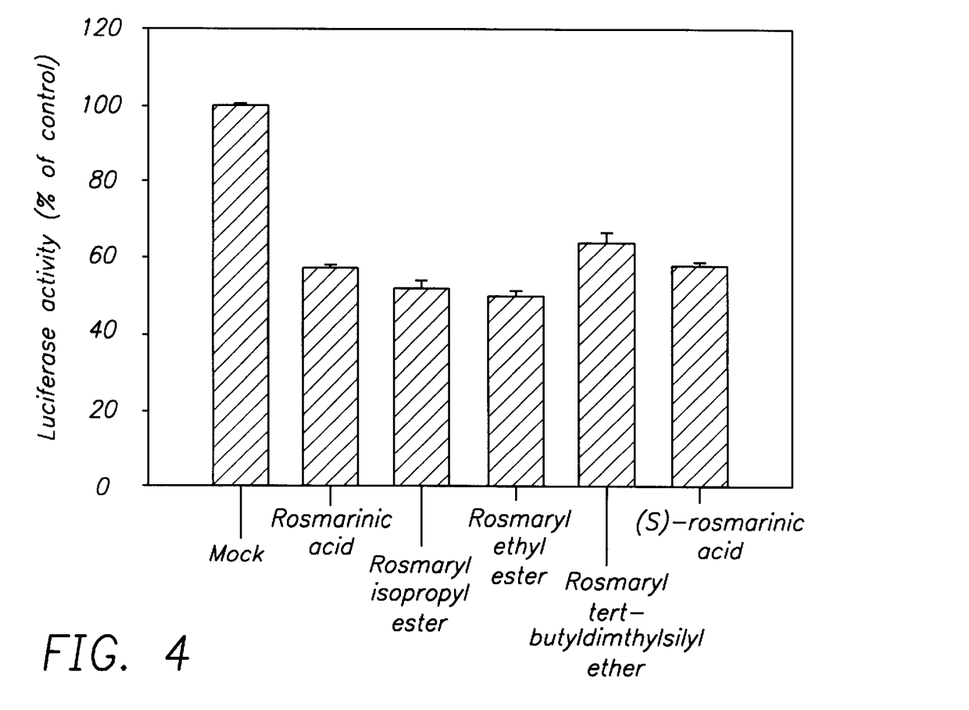
FIG. 4 shows the suppressive effect of the derivatives of rosmarinic acid or (S)-rosmarinic acid on TCR-stimulated T cell activation.

Rosmarinic acid inhibited the TCR-induced IL-2 gene expression more efficiently than other immunosuppressants did (see FIG. 3). Furthermore, the luciferase activities in the experiments using derivatives of rosmarinic acid such as rosmarinyl isopropyl ester, rosmarinyl ethyl ester and (S)-rosmarinyl bis(tert-butyldimethylsilyl)ether and (S)-rosmarinic acid were inhibited as much as rosmarinic acid (see FIG. 4).

Since rosmarinic acid and derivatives thereof effectively suppress T cell activation, they can be used to treat and/or prevent the diseases involved in T cell-mediated immune responses, such as autoimmune diseases, chronic inflammatory diseases as well as transplantation rejection and GVHD.

Example 10

Inhibition of T cell proliferation

As Lck is a T cell-specific tyrosine kinase exerting its activity for T cell activation and proliferation, in present invention, the inhibitory activity of rosmarinic acid to T cell proliferation was tested. The mixed lymphocyte reaction (MLR) test described below may be used to demonstrate that the compounds of this invention have the ability to suppress or inhibit an immune cell reaction. The MLR is used for the determination of transplantation compatibility between the donor (graft) and the recipient (Park and Good, p71, in Tissue typing and organ Transplantation, 1973, Academic Press Inc., N.Y.). The MLR, in which immune response is elicited by mixing two kinds of lymphocytes isolated from different species or individuals, represents the activity of the immune response by growth rates of cells.

Splenocytes ($1 \times 10^5$/well) isolated from Balb/c and C57BL/6 mice were mixed and incubated at 37° C. in a humidified incubator. At 5th day, [methyl-$^3$H]-thymidine (0.5 μCi/well) was added to the cultures, and then the incorporated amounts into the cultures were measured next day. During all procedure, Cyclosporin A, rosmarinic acid, derivatives thereof or (S)-rosmarinic acid was treated at an indicated concentration.

Rosmarinic acid utilized in the present invention inhibited T cell proliferation in a dose-related fashion over a range from $10^{-1}$ to 1000 nM (FIG. 5), whereas rosmarinyl isopropyl ester, rosmarinyl ethyl ester, (S)-rosmarinyl bis(tert-butyldimethylsilyl)ether and (S)-rosmarinic acid from 1 nM to 1000 nM.

The MLR is an in vitro immune response. Inhibition of the MLR immune response is a standard assay used in the field of immunology, which is considered to be indicative of in vivo immunosuppressive activity. In particular, activity in the MLR indicates that rosmarinic acid and derivatives thereof should be effective in preventing organ transplantation rejection and GVHD. Thus, in view of the results presented in the application, rosmarinic acid and derivatives thereof are expected to be efficacious in treating these diseases.

Example 11
Inhibition of immune response in vivo

In vivo test procedure evaluating the immunosuppressive activity was performed using contact hypersensitivity response to DNEB (2,4-dinitroflourobenzene). Contact sensitivity to DNFB has been extensively studied and characterized in the mouse to determine the regulatory mechanisms involved in cell-mediated immune responses (Claman et al., Immunol. Rev. 50:105, 1980; Young and Young, "Cutaneous Models of Inflammation for the evaluation of topical and systemic pharmacological agents" in Pharmacological a methods in the control of inflammation (Chang and Lewis, Eds.), Alan R. Liss, Inc., N.Y., York, pp215–231, 1989). This is an antigen-specific T cell-mediated inflammatory response that represents delayed-type hypersensitivity (DTH) reactions seen in both humans and other mammals. The contact sensitivity animal model is used routinely in many laboratories for pharmacological screening of anti-inflammatory agents and agents for the treatment of autoimmune diseases.

Sensitization and elicitation of contact sensitivity reaction were performed as described by Schenius et al.(Scheynius, 1804, JI). The procedure is summarized as following. Balb/c female mice were used at 8 weeks of age. Twenty μl of 0.5% DNFB (Sigma Chemical Co.) in 4:1 diluted acetone: olive oil (Sigma Chemical Co.) was painted on each shaved abdominal skin for 2 successive days. Four days later, the mice were challenged by applying 10 μl of 0.2% DNFB in the same vehicle to each side of each ear. Cydosporin A and rosmarinic acid were treated through intramuscular administration at the indicated doses from 0 to 5 day. Ear thickness was measured using engineer's micrometer (Mitutoyo Co. Mfg. Ltd., Tokyo) 24 h after postchallenge.

The treatment with rosmarinic acid (5–50 mg/kg/day) or cyclosporin A on 6 consecutive days during the induction phase dose-dependently suppressed the DNFB-induced contact hypersensitivity (FIG. 6). Rosmarinyl isopropyl ester, rosmarinyl ethyl ester, (S)-rosmarinyl bis(tert-butyldimethylsilyether and (S)-rosmarinic acid also showed dose-dependent suppression. The present results show that rosmarinic acid and derivatives thereof can suppress the helper T cell function and memory T cell formation in vivo.

Based on the results of these standard pharmacological test procedures, the compounds are useful in the treatment of transplantation rejection such as heart, kidney, liver, bone marrow and skin transplants; autoimmune diseases such as lupus, rheumatoid arthritis, diabetes mellitus, myasthenia gravis, multiple sclerosis and psoriasis; diseases of inflammation such as dermatitis, eczema, seborrhea and inflammatory bowel disease; and fungal infections.

Example 12
Inhibition of graft rejection

The abilities of rosmarinic acid and derivatives thereof to induce immunosuppression were established in vivo standard pharmacological test procedures. In vivo procedure evaluated the survival time of a skin graft.

Experimental allograft rejection was performed by grafting allogeneic C57BL/6 (H-2b) mouse tail-skin onto Balb/c (H-2d) recipient mice. Rosmarinic acid and derivative thereof were administered intramuscularly from the day of the transplantation until rejection. Cyclosporin A was used as test control, whereas untreated recipients serve as rejection control. Full-thickness donor (C57BL/6) tail skin grafts (square pieces 2.0×2.0 cm) were transplanted onto the lateral thorax of recipient mice (Balb/C) and covered with sterile bactericidal gauze. The entire chest was then wrapped with an elastic bandage. Either rosmarinic acid, derivatives thereof (15 mg/kg/day) or Cydosproin A (50 mg/kg/day) of liposomal preparation was intramuscularly administered daily to the transplanted animal at the mentioned doses until rejection. Skin graft were monitored daily after the removal of the bandage on day 6. Rejection was defined as more than 90% necrosis of the graft epithelium.

As shown in table 1, rejection of allografts in the empty vehicle-treated control group started on day 7. About 50% of the allografts in the control group were rejected on day 9. Rosmarinic acid and derivatives thereof at doses of 15 mg/kg/day showed significant prolonged effect of skin graft survival. The mean survival time (MSI) of skin grafts was 9.6 days in the control group and was 14.0 days for the group of mice treated with rosmarinic acid at 15 mg/kg/day (P <0.01). Cydosporin A was also effective at doses of 50 mg/kg (MST=13.4 days) similar with previous reports, in this system.

These results of this in vivo standard pharmacological test procedure showed that treatment of rosmarinic add or derivatives thereof induced immunosuppression, and thereby prevented skin graft rejection.

In addition, rosmarinic acid or derivatives thereof utilized in the present invention synergize with Cycolsporin A in inhibiting skin graft rejection in vivo. Their dose-lowering synergism with Cyclosporin A means that in therapeutic immunosuppression they can be expected to avoid side effects.

TABLE 1

| Drug | Dose from Day 0 to 12 (mg/kg/day) | Graft survival time (days) | MST ± SD (days) |
|---|---|---|---|
| Empty vehicle | — | 7, 9, 10, 10, 11 | 9.4 ± 1.5 |
| Cyclosporin A | 50 (p.o.) | 13, 14, 14, 14, 14 | 13.8 ± 0.5 |
| Cyclosporin A | 50 (i.m.) | 13, 13, 13, 14, 14 | 13.4 ± 0.5 |
| Rosmarinic acid | 25 (i.m.) | 16, 17, 18, 18, 25 | 18.8 ± 3.6 |
| Rosmarinic acid | 15 (i.m.) | 13, 13, 14, 15, 15 | 14.0 ± 1.0 |
| Rosmarinyl isopropyl ester | 15 (i.m.) | 13, 13, 13, 15, 17 | 14.2 ± 1.8 |
| Rosmarinyl ethyl ester | 15 (i.m.) | 12, 14, 14, 15, 17 | 14.4 ± 1.8 |
| (S)-Rosmarinyl bis(tert-butyldimethylsilyl)ether | 15 (i.m.) | 12, 12, 13, 13, 16 | 13.2 ± 1.6 |
| (S)-rosmarinic acid | 15 (i.m.) | 13, 14, 15, 15, 17 | 14.8 ± 1.5 |
| Cyclosproin A + rosmarinic acid | 17 + 10 (i.m.) | 14, 14, 15, 15, 17 | 15.0 ± 1.4 |

Example 13
Inhibition of cytokine gene expression in grafted tissues

According to one important aspect of the invention, it has been discovered that rosmarinic acid has the ability to suppress cytokine genes expressed at higher level in allograft tissues. The implications of this finding, for use in immunosuppression therapy and for use in treatment to other diseases caused by the elevation of these cytokines are discussed in this Example.

The ability of rosmarinic acid to suppress the production of cytokines was examined using the method RT-PCR. Balb/c recipients transplanted from C57BL/6 donor were killed at 7 day after the subcapsular kidney transplantation. Renal allografts were harvested and total cellular RNA was extracted and analyzed for the expression of various cytokine mRNA. Using a serniquantitative PCR method, we temporally analyzed mRNA levels of IL-1β, IL-2, IL-4, IL-6 and IFN-γ.

We determined the effect of rosmarinic acid (daily dose; 25 mg/kg/day) as well as Cyclosporin A (daily dose; 50 mg/kg/day) administered by intramuscular injection for 7 days. RT-PCR assays used to detect cytoline messages showed that rosmarinic acid markedly inhibited IL-2, IL-4, IFN-γ, IL-6 and IL-1β MRNA transcription in allograft transplants, whereas Cyclosporin A inhibited the expression of IL-2, IFN-γ and IL-1β. The cytokine levels of PCR products were normalized by β-actin mRNA used as a control. IL-4 and IL-6 were significantly reduced by rosmarinic acid but not by Cydosporin A implying that rosmarinic acid suppressed both Th1 and Th2 cytokine expression whereas cyclosporin A can mainly inhibit Th1 cytokines. For IL-2 and IL-1β suppression, rosmarinic acid exerted more potent activity than that of Cyclosporin A. These observations strongly suggested that rosmarinic acid can be a prospective immunosuppressant which affects various immune responses related to graft rejection or T cell-mediated immunopathologies, more extensively.

1) Mouse subcapsular kidney transplantation

Kidney fragments (C57BL/6) were transplanted to allogeneic mice (Balb/C) using subcapsular kidney transplantation technique. After transplantation, rosmarinic acid (25 mg/kg/day) or Cyclosporin A (50 mg/kg/day) formulated with olive oil (Sigma) was intramuscularly injected into the transplanted mice daily for 7 days.

2) Measurement of cytokine mRNA using semi-quantitative RT-PCR

The kidney grafts removed from the transplanted recipients treated with rosmarinic acid (25 mg/kg/day) for 7 days were immediately frozen in liquid nitrogen. Total RNA from the grafts was isolated using TRIZOL® LS Reagent (Life Technologies), incubated at room temperature for 15 min after addition of chloroform, extracted with phenol/chloroform, and precipitated with isopropanol. Isolated total RNA was then quantitated spectrophotometrically. Total RNA from the graft (1 μg) was performed using Titan™ One Tube RT-PCR System (BM) according to the manufacture's protocol. The PCR was done in a 50 μl volume containing 1× RT-PCR buffer with $Mg^{2+}$, 0.2 mM each dNTP(dATP, dGTP, dCTP and dTTP), 10U RNase inhibitor, enzyme mix (AMV and Expand™ High Fidelity PCR-System), 5 mM DTT solution and 0.4 μM appropriate primer pair. Primer sequences for IL-2, IFN-γ, IL-4, IL-6, IL-1β and β-actin were obtained from previous reports. The PCR products of IL-2, IFN-γ, IL-4, IL-6, IL-1β and β-actin are 226, 336, 222, 229, 320 and 568. The number of amplification cycles was 25. An aliquot (15 μl) of the PCR product was electrophoresed on 2% agarose gel, and amplified DNA fragments were stained with ethidium bromide.

3) Primers

The PCR primers are described by SEQ ID NO: 1 to 12. Primers was named for the corresponding gene: m indicates mouse; this is followed by the gene name; F represents forward orientation and R does reverse. For example, IL-2F represents the forward primer used in the PCR of IL-2. Annealing temperatures for all the primers were 52° C., except for 56° C. for β-actin.

Example 14
Parenteral administration test for acute toxicity using rat

We carried out following experiment to find out the acute toxicity of rosmarinic acid and derivatives thereof.

Acute toxicity was examined using 6week-old SPF SD type rat. As liposomal form, I g/kg of rosmarinic acid, rosmarinyl isopropyl ester, rosmarinyl ethyl ester, (S)-rosmarinyl bis(tert-butyldimethylsilyl)ether or (S)-rosmarinic acid was intramuscularly injected into two mice per experimental group. After injection, mice were observed in terms of clinic symptom and change in weights of mice, and brought to blood test and autopsy so as to investigate the abnormalities of abdominal and thoracic organs. As a result, all tested animals were survived, and there was no striking clinic symptom, change in weights or other toxic effect. All the examined compounds did not elicit any toxic effect when injected to rats within the range of 1 g/kg, thus proved to be safe compounds for parenteral administration.

Industrial Applicability

As disclosed by the preferred embodiments, rosmarinic acid and derivatives thereof inhibit the binding to and the function of Lck SH2 domain. This inhibitory effect of rosmarinic acid and derivatives thereof leads to the modification of calcium signal transduction system in T cells; the suppression of IL-2 gene expression in T cells; the suppression of immune responses both in vitro and in vivo; the suppression of graft rejection; and the suppression of cytokine gene expression in grafted tissues. Thus, rosmarinic acid and derivatives thereof are useful for the inhibition of binding to Lck SH2 domain, the suppression of cytokine-mediated immune responses, and the suppression of graft rejection, autoimmune diseases and inflammatory diseases. Since rosmarinic acid and derivatives thereof selectively inhibit the SH2 domain of Lck, a T cell-specific protein, they evoke less side effects on patients than the established immunosuppressants.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for suppressing an immune response for treatment, prevention, or diagnosis of rejection of transplanted organ or tissue, chronic rejection, or graft-versus-host disease; for treatment, prevention, or diagnosis of autoimmune disease; or for treating a condition characterized by elevated levels of IL-1β, IL-4 or IL-6; comprising administering a rosmarinic acid, a derivative thereof or *Prunella vulgaris* extract.

2. The method of claim 1, wherein the rosmarinic acid is employed in the form of enantiomer or diastereomer.

3. The method of claim 1, wherein the derivative is selected from the group comprising rosmarinyl isopropyl ester, rosmarinyl ethyl ester, and (S)-rosmarinyl bis(tert-butyldimethylsilyl)ether.

4. The method of claim 1, wherein the transplanted organ or tissue includes kidney, heart, liver, lung, bone marrow, pancreas or islet cells thereof, cornea, small bowel, skin, or heart valve.

5. The method of claim 1, wherein the autoimmune disease includes lupus, rheumatoid arthritis, diabetes mellitus, myasthenia gravis, multiple sclerosis or psoriasis.

6. The method of claim 1, wherein the condition characterized by elevated levels of IL-1β, IL-4 or IL-6 is selected from the group comprising leukemia, hepatitis, increased cartilage absorption, HIV infection, Alzheimer's disease, muscle breakdown, meningitis, microbacterial infections, thrombosis, arteriosclerotic depositions, elevated fat level, and joint destruction.

7. The method of claim 1, further comprising administering at least one additional immunosuppressant.

8. The method of claim 7, wherein the additional immunosuppressant is selected from the group comprising cyclosporin A and derivatives thereof, FK-506 and derivatives thereof, mycophenolic acid and 2-(N morpholino)ethyl ester thereof, mycophenolate mofetil, azathioprine, corticosteroids, reflunomide, cydophosphamide, rapamvcin, OKT-3, ATG, 15-deoxyspergualin, mizoribine, misoprostol, methotrexate, anti-interleukine-2 receptor antibodies and anti-lymphocyte/thymocyte antisera.

9. A method for inhibiting an SH2 domain, using a rosmarinic acid, a derivative thereof or *Prunella vulgaris* extract.

10. The method of claim 9, wherein the SH2 domain is a lymphocyte cell kinase (Lck) SH2 domain.

11. The method of claim 9, wherein the rosmarinic acid is employed in the form of enantiomer or diastereomer.

12. The method of claim 9, wherein the derivative is selected from the group comprising rosmarinyl isopropyl ester, rosmarinyl ethyl ester, and (S)-rosmarinyl bis(tert-butyldimethylsilyl)ether.

13. The method of claim 9, wherein the method for inhibiting an SH2 domain is used for treatment, prevention, or diagnosis of rejection of transplanted organ or tissue, chronic rejection, or graft-versus-host disease.

14. The method of claim 13, wherein the transplanted organ or tissue includes kidney, heart, liver, lung, bone marrow, pancreas or islet cells thereof, cornea, small bowel, skin, or heart valve.

15. The method of claim 9, wherein the method for inhibiting an SH2 domain is used for treatment, prevention, or diagnosis of autoimmune disease.

16. The method of claim 15, wherein the autoimmune disease includes lupus, rheumatoid arthritis, diabetes mellitus, myasthenia gravis, multiple sclerosis or psoriasis.

17. The method of claim 9, wherein the method for inhibiting an SH2 domain is used for treating a condition characterized by elevated levels of IL-1β, IL4 or IL-6.

18. The method of claim 17, wherein the condition is selected from the group comprising leukemia, hepatitis, increased cartilage absorption, HIV infection, Alzheimer's disease, muscle breakdown, meningitis, microbacterial infections, thrombosis, arteriosclerotic depositions, elevated fat level, and joint destruction.

19. The method of claim 9, further using at least one additional immunosuppressant.

20. The method of claim 19, wherein the additional immunosuppressant is selected from the group comprising cyclosporin A and derivatives thereof, FK-506 and derivatives thereof, mycophenolic acid and 2-(N-morpholino)ethyl ester thereof, mycophenolate mofetil, azathioprine, corticosteroids, reflunomide, cyclophosphamide, rapamycin, OKT-3, ATG, 15-deoxyspergualin, mizoribine, misoprostol, methotrexate, anti-interleukine-2 receptor antibodies and anti-lymphocyte/thymocyte antisera.

* * * * *

SEQUENCE LISTING

<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: mIL-2F, forward primer in the PCR of mouse IL-2 gene

<400> SEQUENCE: 1
gcaggatgga gaattacagg a                                                21

<210> SEQ ID NO 2
<211> LENGTH: 20
<212> TYPE: DNA
<213> ORGANISM: Artificial Sequence
<220> FEATURE:
<223> OTHER INFORMATION: mIL-2R, reverse primer in the PCR of mouse IL-2
      gene

<400> SEQUENCE: 2
tcagagccct ttagttttac                                                  20

<210> SEQ ID NO 3
<211> LENGTH: 20
<212> TYPE: DNA
<213> ORGANISM: Artificial Sequence
<220> FEATURE:
<223> OTHER INFORMATION: mIL4F, forward primer in the PCR of mouse IL-4
      gene

<400> SEQUENCE: 3
acaggagaag ggacgccatg                                                  20

<210> SEQ ID NO 4
<211> LENGTH: 20
<212> TYPE: DNA
<213> ORGANISM: Artificial Sequence
<220> FEATURE:
<223> OTHER INFORMATION: mIL-4R, reverse primer in the PCR of mouse IL-4
      gene

<400> SEQUENCE: 4
gcagcttatc gatgaatcca                                                  20

<210> SEQ ID NO 5
<211> LENGTH: 23
<212> TYPE: DNA
<213> ORGANISM: Artificial Sequence
<220> FEATURE:
<223> OTHER INFORMATION: mIL-6F, forward primer in the PCR of mouse IL-6
      gene

<400> SEQUENCE: 5 acaaagcca gagtccttca gag                                               23

<210> SEQ ID NO 6
<211> LENGTH: 22
<212> TYPE: DNA
<213> ORGANISM: Artificial Sequence
<220> FEATURE:
<223> OTHER INFORMATION: mIL-6R, reverse primer in the PCR of mouse IL-6
      gene

<400> SEQUENCE: 6
ctagctttgc cgagtagatc tc                                               22

<210> SEQ ID NO 7
<211> LENGTH: 23
<212> TYPE: DNA
<213> ORGANISM: Artificial Sequence
<220> FEATURE:
<223> OTHER INFORMATION: mIFN-gammaF, forward primer in the PCR of mouse
      IFN-gamma gene

<400> SEQUENCE: 7

-continued

```
ggaggaactg gcaaaaggat ggt                                          23

<210> SEQ ID NO 8
<211> LENGTH: 21
<212> TYPE: DNA
<213> ORGANISM: Artificial Sequence
<220> FEATURE:
<223> OTHER INFORMATION: mIFN-gammaR, reverse primer in the PCR of mouse
      IFN-gamma gene

<400> SEQUENCE: 8
ttgggacaat ctcttcccca c                                            21

<210> SEQ ID NO 9
<211> LENGTH: 22
<212> TYPE: DNA
<213> ORGANISM: Artificial Sequence
<220> FEATURE:
<223> OTHER INFORMATION: mIL-1betaF, forward primer in the PCR of mouse
      IL-1beta gene

<400> SEQUENCE: 9
ttgaagaaga gcccatcctc tg                                           22

<210> SEQ ID NO 10
<211> LENGTH: 20
<212> TYPE: DNA
<213> ORGANISM: Artificial Sequence
<220> FEATURE:
<223> OTHER INFORMATION: mIL-1betaR, reverse primer in the PCR of mouse
      IL-1beta gene

<400> SEQUENCE: 10
gatccacact ctccagctgc                                              20

<210> SEQ ID NO 11
<211> LENGTH: 24
<212> TYPE: DNA
<213> ORGANISM: Artificial Sequence
<220> FEATURE:
<223> OTHER INFORMATION: beta-actinF, reverse primer in the PCR of mosue
      beta-actin gene

<400> SEQUENCE: 11
cgacgaggcc cagagcaaga gagg                                         24

<210> SEQ ID NO 12
<211> LENGTH: 30
<212> TYPE: DNA
<213> ORGANISM: Artificial Sequence
<220> FEATURE:
<223> OTHER INFORMATION: beta-actinR, reverse primer in the PCR of mosue
      beta-actin gene

<400> SEQUENCE: 12
cgtcaggcag ctcatagctc ttctccaggg                                   30
```